United States Patent
Cho et al.

(10) Patent No.: US 12,370,152 B2
(45) Date of Patent: Jul. 29, 2025

(54) PHARMACEUTICAL COMPOSITION FOR PREVENTING OR TREATING METABOLIC DISEASES

(71) Applicant: INDUSTRY ACADEMIC COOPERATION FOUNDATION CHOSUN UNIVERSITY, Gwangju (KR)

(72) Inventors: Gwang Won Cho, Gwangju (KR); Nagarajan Maharajan, Gwangju (KR)

(73) Assignee: INDUSTRY ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 308 days.

(21) Appl. No.: 17/967,273

(22) Filed: Oct. 17, 2022

(65) Prior Publication Data

US 2023/0190682 A1 Jun. 22, 2023

(30) Foreign Application Priority Data

Oct. 19, 2021 (KR) ........................ 10-2021-0139596

(51) Int. Cl.
| | | |
|---|---|---|
| *A61K 31/125* | (2006.01) | |
| *A23L 33/00* | (2016.01) | |
| *A23L 33/10* | (2016.01) | |
| *A61P 1/16* | (2006.01) | |
| *A61P 3/04* | (2006.01) | |
| *A61P 3/06* | (2006.01) | |
| *A61P 3/10* | (2006.01) | |

(52) U.S. Cl.
CPC ............ *A61K 31/125* (2013.01); *A23L 33/10* (2016.08); *A23L 33/40* (2016.08); *A61P 1/16* (2018.01); *A61P 3/04* (2018.01); *A61P 3/06* (2018.01); *A61P 3/10* (2018.01)

(58) Field of Classification Search
CPC ..... A61K 31/125; A61K 31/122; A23L 33/10; A23L 33/40; A61P 1/16; A61P 3/04; A61P 3/06; A61P 3/10; A61P 3/00; A61P 9/10; A23V 2002/00; A23V 2200/326; A23V 2200/328; A23V 2200/332
See application file for complete search history.

(56) References Cited

FOREIGN PATENT DOCUMENTS

| KR | 10-2299407 B1 | 9/2021 | |
|---|---|---|---|
| WO | WO 2007/003521 A2 * | 1/2007 | ........... C07D 237/28 |

OTHER PUBLICATIONS

Notice of Allowance issued on Mar. 5, 2025 from Korean Patent Office in a counterpart Korean Patent Application No. 10-2021-0139596 (all the cited references are listed in this IDS.) (English translation is also submitted herewith.).

Mei-Chi Chang et al., "Effects of Camphorquinone on Cytotoxicity, Cell Cycle Regulation and Prostaglandin E2 Production of Dental Pulp Cells: Role of ROS, ATM/Chk2, MEK/ERK and Hemeoxygenase-1", PLoS One, vol. 10, 2015, pp. 1-20, DOI: 10.1371/journal.pone.0143663.

Rahul A. Datar et al., "Effects of sub-toxic concentrations of camphorquinone on cell lipid metabolism", Journal of Biomaterials Science, vol. 16, Issue 10, 2005, pp. 1293-1302, https://doi.org/10.1163/156856205774269557 (see the abstract).

* cited by examiner

*Primary Examiner* — Joseph K McKane
*Assistant Examiner* — David M Shim
(74) *Attorney, Agent, or Firm* — The PL Law Group, PLLC

(57) ABSTRACT

A method for preventing or treating metabolic diseases includes administering a composition including a compound represented by Formula 1 or a pharmaceutically acceptable salt thereof to a subject in need thereof. Thereby, it is possible to inhibit increases in body weight and liver fat weight due to a high-calorie diet, and decrease an accumulation of fat in the liver tissue, as well as modulate gene expression related to fat metabolism, and ultimately exhibit excellent preventive and therapeutic effects on metabolic diseases.

4 Claims, 10 Drawing Sheets

Specification includes a Sequence Listing.

PHARMACEUTICAL COMPOSITION FOR PREVENTING OR TREATING METABOLIC DISEASES

CROSS-REFERENCE TO RELATED APPLICATIONS AND CLAIM OF PRIORITY

This application claims the benefit under 35 USC § 119 of Korean patent Application No. 10-2021-0139596, filed on Oct. 19, 2021, in the Korean Intellectual Property Office, the entire disclosure of which is incorporated herein by reference for all purposes.

BACKGROUND

1. Field of the Invention

The present invention relates to a pharmaceutical composition for preventing or treating metabolic diseases. In addition, the present invention relates to a food composition for preventing or improving metabolic diseases.

2. Description of the Related Art

Metabolic disease is a disease in which risk factors of death, such as obesity, diabetes, insulin resistance, fatty liver, dyslipidemia, arteriosclerosis, or complications thereof exist together, and is also known as 'metabolic syndrome'. Recently, it is known that the incidence of metabolic diseases is rapidly increasing not only in Korea, but also in the United States and Western European nations.

Obesity means a condition in which intake and consumption of energy are not balanced due to lifestyle habits or genetic causes, and excess energy is accumulated as fat, thus to cause an abnormal increase in the body fat and lead to metabolic abnormalities. Obesity is becoming more common among modern people due to the improvement of the standard of living according to economic development, and is a major cause in regard to increasing the risk of hypertension, hyperlipidemia, arteriosclerosis, heart disease, diabetes mellitus and the like.

Diabetes mellitus is a disease in which an amount of insulin secretion is insufficient or insulin function is not operating normally, and features hyperglycemia with an increase in the glucose concentration in the blood, as well as causes various symptoms and signs due to the hyperglycemia, including the excretion of glucose in the urine. In addition, diabetes mellitus is a disease that causes vascular disorders and functional disorders of nerves, kidneys, and retinas, etc. over a long period of time, and thereby causing loss of life.

Dyslipidemia refers to a state where concentrations of total cholesterol, neutral fat, and LDL cholesterol in the blood are high or the concentration of HDL cholesterol is low. When lipid components such as LDL cholesterol or neutral fats in the blood are increased, blood flow is not smooth and lipid components are adhered to the arterial wall, thereby causing chronic inflammation, and leading to arteriosclerosis in which the arterial wall is narrowed and the blood vessel is hardened. In the long term, blood clots resulting from dyslipidemia block the coronary arteries or blood vessels in the brain, thereby causing myocardial infarction, stroke, cerebral infarction or the like.

Fatty liver refers to a pathological condition in which fat exceeds 5% or more of total liver weight. Liver disease including fatty liver is known to be the second most serious disease after cancer among the causes of death of adult populations in their 40s and 50s in advanced countries. In particular, nonalcoholic fatty liver disease (NAFLD) continues to increase due to excessive nutrition associated with a high-fat and high-carbohydrate intake of modern people. The nonalcoholic fatty liver disease refers to a wide range of liver diseases including nonalcoholic simple steatosis, nonalcoholic steatohepatitis (NASH), and other liver diseases progressing to nonalcoholic fatty liver-associated cirrhosis. The nonalcoholic fatty liver disease is characterized by having accumulation of fat (fat infiltration) in hepatocytes. The nonalcoholic simple steatosis may progress to nonalcoholic steatohepatitis. Fat accumulation in the nonalcoholic steatohepatitis is known to be associated with varying extents of liver inflammation and scarring, and in many cases, insulin resistance, dyslipidemia and hypertension.

Drugs for treating these metabolic diseases have been developed, but a satisfactory treatment method or drug has not yet been developed. Thereby, development of a new material capable of preventing or treating metabolic diseases as described above without side effects is required.

SUMMARY

An object of the present invention is to provide a pharmaceutical composition for preventing or treating metabolic diseases.

Another object of the present invention is to provide a food composition for preventing or improving metabolic diseases.

To achieve the above objects, the following technical solutions are adopted in the present invention.

1. A pharmaceutical composition for preventing or treating metabolic diseases, including a compound represented by Formula 1 below or a pharmaceutically acceptable salt thereof:

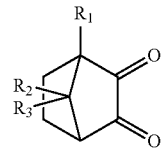

[Formula 1]

(wherein $R_1$ is H or $C_1$ to $C_6$ alkyl, $R_2$ is H or $C_1$ to $C_6$ alkyl, and $R_3$ is H or $C_1$ to $C_6$ alkyl).

2. The pharmaceutical composition according to the above 1, wherein the metabolic disease is at least one selected from the group consisting of obesity, diabetes, dyslipidemia, fatty liver, arteriosclerosis, stroke, hyperglycemia, insulin resistance disease and hyperinsulinemia.

3. The pharmaceutical composition according to the above 1, wherein R1 is C1 alkyl, $R_2$ is C1 alkyl, and $R_3$ is C1 alkyl.

4. A food composition for preventing or improving metabolic diseases, including a compound represented by Formula 1 below or a sitologically acceptable salt thereof:

[Formula 1]

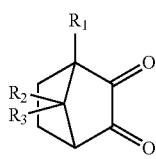

(wherein $R_1$ is H or C1 to C6 alkyl, $R_2$ is H or C1 to C6 alkyl, and $R_3$ is H or C1 to C6 alkyl).

The compositions of the present invention may inhibit increases in body weight and liver fat weight due to a high-calorie diet, and may decrease an accumulation of fat in the liver tissue. In addition, the compositions of the present invention may modulate gene expression related to fat metabolism. Moreover, the compositions of the present invention may reduce blood glucose and improve glucose tolerance.

The compositions of the present invention exhibit excellent preventive and therapeutic effects on metabolic diseases such as obesity, diabetes, hyperlipidemia, hypertriglyceridemia, liver disease, arteriosclerosis, stroke, myocardial infarction, cardiovascular disease, hyperglycemia, insulin resistance disease, hyperinsulinemia and the like.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
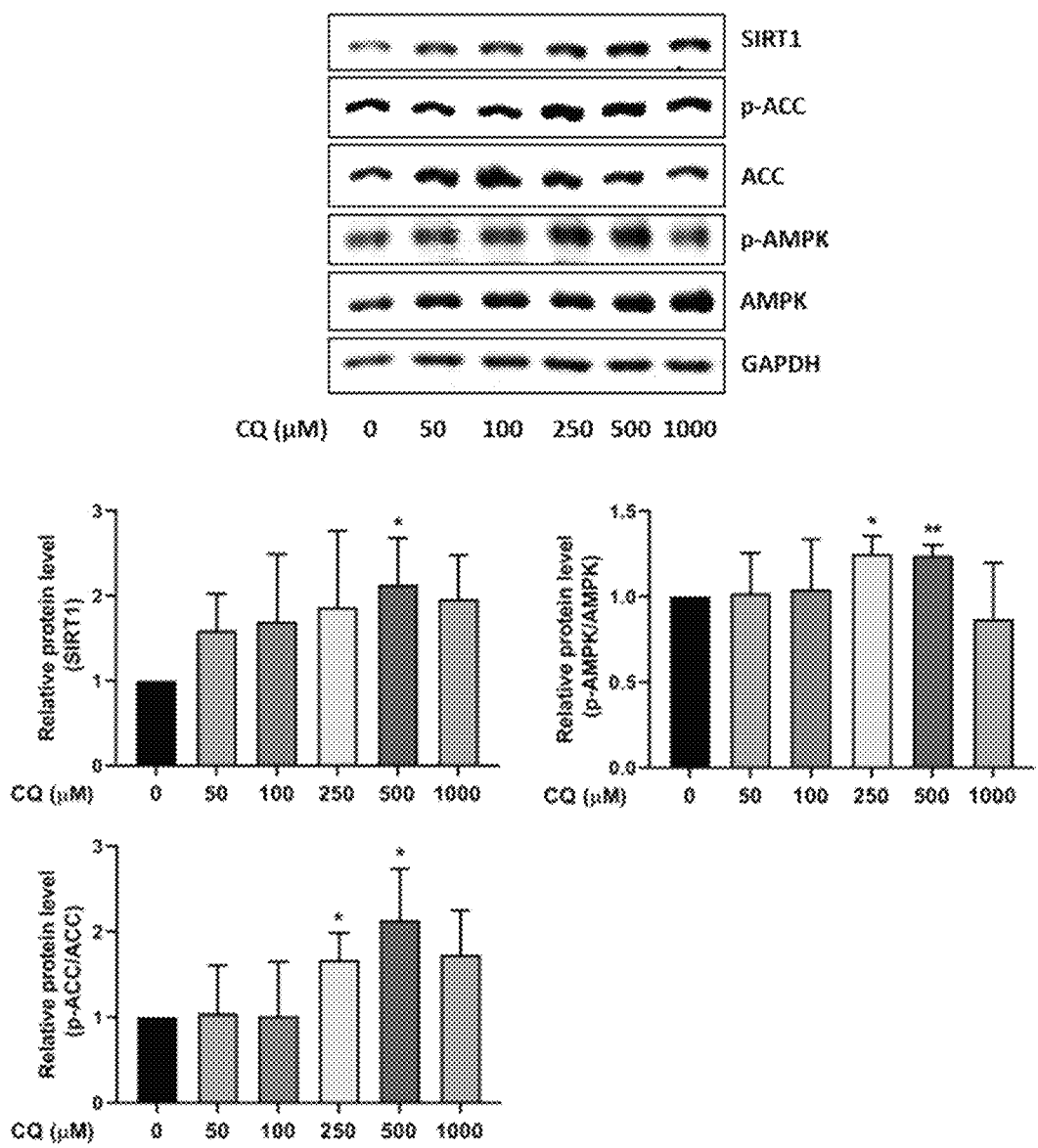
FIG. 1 illustrates results of confirming that camphorquinone increases the activation of AMP-activated protein kinase (AMPK), Sirtuin 1 (SIRT1) and acetyl-CoA carboxylase (ACC) in HepG2 cells (*$P<0.05$ and **$P<0.01$)

Hereinafter, the present invention will be described.

The present invention provides a pharmaceutical composition for preventing or treating metabolic diseases, which includes a compound represented by Formula 1 below or a pharmaceutically acceptable salt thereof:

[Formula 1]

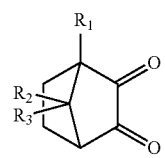

(wherein $R_1$ is H or C1 to C6 alkyl, $R_2$ is H or C1 to C6 alkyl, and $R_3$ is H or C1 to C6 alkyl).

In Formula 1 above, $R_1$ may be H or C1 to C6 alkyl. In Formula 1 above, $R_1$ may be H or C1 to C3 alkyl.

In Formula 1 above, $R_2$ may be H or C1 to C6 alkyl. In Formula 1 above, $R_2$ may be H or C1 to C3 alkyl.

In Formula 1 above, $R_3$ may be H or C1 to C6 alkyl. In Formula 1 above, $R_3$ may be H or C1 to C3 alkyl.

In Formula 1 above, $R_1$ may be H or C1 to C3 alkyl, $R_2$ may be H or C1 to C3 alkyl, and $R_3$ may be H or C1 to C3 alkyl.

The compound represented by Formula 1 may be a material extracted from natural substances, or may be chemically synthesized.

According to one embodiment, in Formula 1 above, $R_1$ may be C1 alkyl, $R_2$ may be C1 alkyl and $R_3$ may be C1 alkyl. In Formula 1, the structure wherein $R_1$ is C1 alkyl, $R_2$ is C1 alkyl and $R_3$ is C1 alkyl represents camphorquinone.

That is, the present invention may provide a pharmaceutical composition for prevention or treatment of metabolic diseases, which includes camphorquinone (CQ, also known as 2,3-bornanedione) or a pharmaceutically acceptable salt thereof.

In Formula 1 above, compounds in which $R_1$, $R_2$ and $R_3$ are each independently C1 to C6 alkyl may have the same matrix and similar substituents, therefore, it is sufficiently predictable that these compounds may show similar functional effects because they may possess similar features in structural or chemical aspects. For example, it is considered that metabolic diseases preventing or treating effects of the compounds in which $R_1$, $R_2$ and $R_3$ are each independently C2 to C6 alkyl may be within a range sufficiently predictable from metabolic disease preventing or treating effects of the compounds in which $R_1$, $R_2$ and $R_3$ are each independently C1 alkyl.

Camphorquinone may be synthesized from camphor as shown in Scheme 1 below.

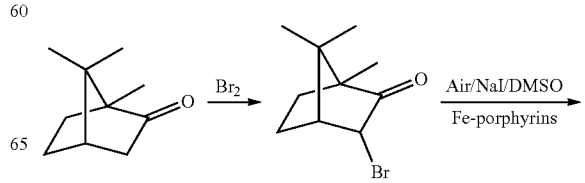

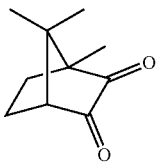

The compositions of the present invention may exhibit effects of decreasing a lipid accumulation in hepatocytes and reducing the body weight and liver weight, and effects of modulating gene expression related to lipid metabolism in hepatocytes. In addition, the compositions of the present invention may exhibit effects of decreasing blood glucose and improving glucose tolerance. The compositions of the present invention may activate AMPK and SIRT1 in hepatocytes. In relation to these effects, the compositions of the present invention may exhibit prophylactic or therapeutic effects on metabolic diseases.

The term "metabolic disease" refers generically to diseases caused by in vivo metabolic disorders.

The metabolic disease may be at least one selected from the group consisting of obesity, diabetes, dyslipidemia, fatty liver, arteriosclerosis, stroke, myocardial infarction, cardiovascular disease, hyperglycemia, insulin resistance disease, and hyperinsulinemia, but it is not limited thereto.

The term "obesity" may mean a state where body fat is excessively accumulated. Based on the standard of obesity, it may be defined as obesity when the body fat is 25% or more of body weight in men and 30 to 35% or more in women. As a general measurement method of obesity, body mass index (BMI), which is expressed as weight (kg)/height $(m)^2$, is widely used.

The term "dyslipidemia" may mean a state where lipid components such as neutral fats, LDL cholesterol, phospholipids and free fatty acids, etc. in the blood are increased or HDL cholesterol is decreased. The dyslipidemia may be, for example, any one or more selected from the group consisting of hyperlipidemia, hyper-LDL cholesterolemia, hypertriglyceridemia and hypo-HDL cholesterolemia.

The term "fatty liver disease (FLD)" is a pathological condition in which fat exceeds 5% or more of the total liver weight, and is associated with metabolic diseases such as obesity, diabetes or the like. The fatty liver may be hepatic steatosis, or nonalcoholic fatty liver disease (NAFLD).

The expression "pharmaceutically acceptable" means characteristics of not impairing physical properties as well as biological activity of a compound are exhibited without arousing significant stimulation in a subject, cell, tissue, etc. to which the compound or a composition including the compound is administered.

The expression "pharmaceutically acceptable salt" refers to a salt prepared using a specific compound according to the present invention, as well as acid or base relatively nontoxic thereto. The pharmaceutically acceptable salt may include, for example, acid addition salts or metal salts.

The acid addition salts may be formed from inorganic acids such as hydrochloric acid, nitric acid, phosphoric acid, sulfuric acid, hydrobromic acid, hydroiodic acid, nitrous or phosphorous acid, aliphatic mono and dicarboxylates, phenyl-substituted alkanoates, hydroxy alkanoates and alkane dioates, and non-toxic organic acids such as aromatic acids, aliphatic and aromatic sulfonic acids. These pharmaceutically non-toxic salts may include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propyolate, oxalate, malonate, succinate, suberate, sebacate, fumarate, maleate, butine-1,4-dioate, nucleic acid-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, β_hydroxybutyrate, glycolate, malate, tartrate, methane sulfonate, propane sulfonate, naphthalene-1-sulfonate, naphthalene-2-sulfonate or mandelate. For example, the acid addition salt may be obtained by dissolving the compound in an excess amount of aqueous acid solution and precipitating the salt using a hydrated organic solvent such as methanol, ethanol, acetone or acetonitrile.

The metal salt may be a sodium, potassium or calcium salt. The metal salt may be prepared using a base, for example, alkali-metal or alkaline earth metal salts may be obtained by dissolving the compound in an excess amount of alkali-metal hydroxide or alkaline earth metal hydroxide solution, filtering the non-dissolved compound salt, and evaporating and/or drying the filtrate.

The term "prevention" refers to a precautionary procedure that includes a slight, substantial or significant reduction in possibility of occurrence or recurrence of disease condition as well as overall prevention, and leads to a reduction in some extent of onset possibility of the disease condition to be prevented or the disease condition recurred or being recurred, wherein the extent of reduction in possibility means at least slight reduction.

The term "treatment" refers to a procedure that includes some extent of alleviation including slight alleviation, substantial alleviation or major relaxation as well as healing, and leads to beneficial effects on a subject or patient suffering from a disease condition to be treated, wherein the extent of relaxation means at least slight relaxation.

The pharmaceutical composition of the present invention may be formulated and used in the form of oral formulations such as powder, granules, tablets, capsules, suspension, emulsion, syrup, aerosol, etc., external applications, suppositories, and sterile injection, but it is not limited thereto.

Carriers, excipients and diluents able to be contained in the composition may include, for example, lactose, dextrose, sucrose, dextrin, maltodextrin, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil, but they are not limited thereto. Such formulations are produced using diluents or excipients such as fillers, extenders, binders, wetting agents, disintegrants, surfactants, etc., which are typically used in the art, but they are not limited thereto.

Solid formulations for oral administration may include tablets, pills, powder, granulates, capsules, etc., without limitation thereof, and such solid formulations may be prepared by admixing the compound as described above with at least one excipient, for example, starch, calcium carbonate, sucrose, lactose, gelatin and the like. Further, other than simple excipients, lubricants such as magnesium stearate, talc, etc. may also be used.

Liquid formulations for oral use may include suspending agents, oral liquids, emulsions, syrup and the like. Other than simple diluents commonly used in the art such as water and liquid paraffin, various excipients such as wetting agents, sweeteners, fragrances, preservatives, etc. may be used. Formulations for parenteral administration may include sterile aqueous solution, non-aqueous solvent, suspending agents, emulsions, freeze-dried preparations, suppositories and the like. The non-aqueous solvents or suspending agents used herein may include propylene glycol, polyethylene glycol, vegetable oil such as olive oil, injectable ester such as ethyl oleate, etc. As a base of the suppository, witepsol, macrogol, tween 60, cacao butter, laurin, glycerogelatin, and the like may be used.

The pharmaceutical composition of the present invention may be administered in a pharmaceutically effective amount. In the present invention, the expression "pharmaceutically effective amount" means an amount sufficient to treat a disease at a reasonable benefit/damage rate applicable to the medical treatment, and effective dose levels may be determined depending on types of disease of the patient, severity, activity of drug, sensitivity to drug, administration time, administration route and rate of release, duration of treatment, factors including concurrent medications, and other factors well known in the medical field. The pharmaceutical composition of the present invention may be administered as an individual therapeutic agent or in combination with other therapeutic agents, may be administered sequentially or simultaneously with conventional therapeutic agents, and may be administered in single or multiple doses. Taking all of the above factors into consideration, it is important to administer the pharmaceutical composition in an amount that can achieve maximum effects with a minimum amount without side effects, which may be easily determined by those skilled in the art.

With regard to the pharmaceutical composition of the present invention, the "effective amount" may vary depending on the age, gender, body weight of a patient. Generally, the composition may be administered in an amount of 1 to 6000 mg, and preferably 60 to 600 mg per 1 kg of body weight once or in three (3) divided doses. However, since the dose may be increased/decreased according to the administration route, severity of disease, gender, body weight, age, etc., the range of the present invention is not particularly limited in any manner by the above administration dose.

In addition, the present invention provides a food composition for preventing or improving metabolic diseases, which includes a compound represented by Formula 1 below or a sitologically acceptable salt thereof:

[Formula 1]

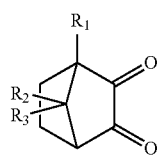

(wherein $R_1$ is H or C1 to C6 alkyl, $R_2$ is H or C1 to C6 alkyl, and $R_3$ is H or C1 to C6 alkyl).

Since the compound represented by Formula 1 and the metabolic diseases have been described above, therefore will not be described in detail.

The expression "sitologically acceptable" means that characteristics of not impairing physical properties as well as biological activity of a compound are exhibited without arousing significant stimulation in a subject, cell, tissue, etc. to which the compound or a composition including the compound is administered.

The expression "sitologically acceptable salt" refers to a salt prepared using a specific compound according to the present invention, as well as acid or base relatively non-toxic thereto. The sitologically acceptable salt may include, for example, acid addition salts or metal salts wherein the acid addition salts and metal salts may be within the above-described range, but they are not limited thereto.

The food composition may be prepared and processed in the form of tablets, capsules, powder, granules, liquid, pills, etc.

The food composition of the present invention may include any conventional food additive. Herein, suitability of the food composition as a food additive is judged on the basis of standards and criteria of corresponding items according to the General Regulations of the Food Additives and General Test Methods approved by the Food and Drug Administration, unless otherwise specified.

The items listed in the General Regulations of the Food Additives include, for example: chemical compounds such as ketones, glycine, calcium citrate, nicotinic acid and cinnamon acid; natural additives such as dark blue pigment, licorice extract, crystalline cellulose, high color pigment and guar gum; and mixed preparations such as sodium L-glutamate preparations, noodle-added alkaline chemicals, preservative preparations, and tar coloring preparations, and the like, but it is not limited thereto.

For example, the food composition in the form of tablets may be produced by mixing the composition with excipients, binders, disintegrants and other additives to prepare a mixture, granulating the mixture in any conventional manner, and then, compression molding the same along with addition of a lubricant or directly compression molding the mixture. Further, the food composition in the form of tablets may contain a flavor enhancer, or the like as necessary.

Among food compositions in the form of capsules, a hard capsule formulation may be produced by filling a typical hard capsule with a mixture of the composition and additives such as excipients, and a soft capsule formulation may be produced by filling a capsule base such as gelatin with a mixture of the composition and additives such as excipients. The soft capsule formulation may further contain a plasticizer such as glycerin or sorbitol, a colorant, a preservative, and the like as necessary.

A food composition in the form of pills may be produced by molding a mixture of the composition and excipients, binders, disintegrants, etc. according to any known method and, if necessary, may be enveloped with white sugar or other enveloping agents. Alternatively, the surface of the food may be coated with specific materials such as starch, talc and the like.

A food composition in the form of granules may be produced by granulating a mixture of the composition and excipients, binders, disintegrants, etc. according to a known method, and may contain a flavoring agent, a flavor enhancer, and the like as necessary.

The food composition may be beverages, meat, chocolate, foods, confectionery, pizza, ramen, other noodles, gums, candy, ice cream, alcoholic beverages, vitamin complexes and dietary supplements.

The food composition may be orally applied for use of nutritional supplements, and the application forms thereof are not particularly limited. For example, for oral administration, daily intake is preferably 5000 mg or less, and more preferably 2000 mg or less. Most preferably, the daily intake ranges from 500 to 1500 mg or is 650 mg. When formulated into capsules or tablets, one capsule or tablet may be administered along with water once a day.

The present invention relates to a method for preventing or treating metabolic diseases.

The method for preventing or treating metabolic diseases may include: administering a composition comprising a compound represented by Formula 1 below or a pharmaceutically acceptable salt thereof to a subject in need thereof:

[Formula 1]

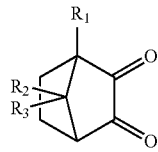

(wherein $R_1$ is H or C1 to C6 alkyl, $R_2$ is H or C1 to C6 alkyl, and $R_3$ is H or C to C6 alkyl).

The subject may include human and/or animals except for the human.

The subject may include subjects who have been diagnosed to have metabolic disease or are at risk for the same, but it is not limited thereto.

Since the compound represented by Formula 1 and the metabolic diseases have been described above, therefore will not be described in detail.

In addition, the present invention provides a composition for activating AMPK or SIRT1, which includes a compound represented by Formula 1 below or a pharmaceutically acceptable salt thereof:

[Formula 1]

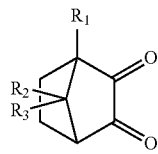

(wherein $R_1$ is H or C1 to C6 alkyl, $R_2$ is H or C1 to C6 alkyl, and $R_3$ is H or C1 to C6 alkyl).

Since the compound represented by Formula 1 have been described above, therefore will not be described in detail.

The composition may be a composition for activating AMPK or SIRT1 in vitro.

Hereinafter, the present invention will be described in detail and illustrated by means of the following examples.

EXPERIMENTAL MATERIAL AND METHOD

1. Chemical and Reagent

Methylthiazolyldiphenyl-tetrazolium bromide (#M2128 MTT) assay; D-glucose (#G7021) and camphorquinone (CQ, #124893; purity 97%) were purchased from Sigma-Aldrich (USA). Compound C was purchased from Calbiochem (Darmstadt, Germany). Radio-immunoprecipitation Assay (RIPA) lysis buffer was purchased from Santa Cruz Biotechnology (USA), and Pierce BCA protein assay kit was purchased from Thermo Fisher Scientific (USA). RNAiso Plus (#9109; Total RNA extraction reagent) and PrimeScript™ II 1st strand cDNA synthesis kit (#6210A) were purchased from Takara Bio Inc. (Japan). Primary antibodies SIRT1 (#sc-74465), p-LKB1, LKB1, p-ERK, ERK and GAPDH (#sc-365062) were purchased from Santa Cruz Biotechnology, Inc. (Dallas, TX, USA). AMPK (#5832), p-AMPK (#2535), ACC (#3662) and p-ACC (#3661) were purchased from Cell Signaling Technology (USA). Appropriate HRP-conjugated secondary antibodies, mouse anti-rabbit (#sc-2357) and mouse anti-goat (#sc-2354) antibodies were purchased from Santa Cruz Biotechnology, Inc. (Dallas, TX, USA) and horse anti-mouse (#7076) antibody was purchased from Cell Signaling Technology (USA). ECL Western blotting detection reagent (RPN2209) was purchased from GE Healthcare (Buckinghamshire, UK).

2. Cell Culture

HepG2 hepatocytes were cultured in low glucose Dulbecco's modified Eagle medium (DMEM) (Gibco, Life Technologies, Grand Island, NY, USA) to which 10% FBS (Gibco, Life Technologies, USA), L-glutamine, and 1% penicillin/streptomycin solution were added. The cells were manipulated in a humidified incubator at 37° C. containing 5% $CO_2$ under a sterile condition. The cells were sub-cultured as soon as they reached confluence. The cells were continuously monitored under a bright-field microscope (Nikon Eclipse TS100, Tokyo, Japan), and the medium was replaced every 3 days. For cell viability assays, the cells were seeded and treated with 0 μM-2000 μM camphorquinone (CQ) for 24 hours, then incubated in MTT solution (0.5 mg/ml) for 2 hours, and then formazan crystals were dissolved using dimethyl sulfoxide (DMSO). Cell viability was evaluated using a spectrophotometer (Multiskan FC, Thermo Fisher Scientific).

3. Preparation and Treatment of Stock Solution of Free Fatty Acids

Free fatty acids (FFA) were prepared from a combination of palmitic acid (PA) and oleic acid (OA). In short, stocks of 100 mM palmitic acid and 100 mM oleic acid dissolved in sodium hydroxide were prepared. These stock solutions were conjugated with 10% BSA (1:9) solution. All stock solutions were stored at −20° C. The cells were seeded and attached to a 6-well plate, then the cells were treated with a mixture of 0.2 mM PA and 0.4 mM OA (1:2) for 24 hours or the same volume of 10% BSA solution for 24 hours. FFA was removed the next day and 500 μM of camphorquinone was added to the mixture and left for 24 hours. Thereafter, the plate was used for protein and oil red staining.

4. Oil Red O Staining

Oil Red O stock solution dissolved in isopropyl alcohol was prepared by magnetic stirring at room temperature for 2 hours, and the prepared solution was stored at room temperature. Then, Oil Red O working solution was prepared by mixing 1.5 parts of stock solution and 1 part of water (3:2), and incubated at 4° C. for 10 minutes. The solution was filtered through a 0.02 μm filter and used within 6 hours. HepG2 cells were treated by the same procedure as in 3. above, and after 24 hours, the cells were washed with sterile PBS, fixed with 4% formaldehyde for 20 minutes, and stained with 0.5% Oil red O dissolved in isopropanol for 3 minutes at room temperature. The cells stained with Oil red O were rinsed with PBS several times to remove excessively stained portions. The stained lipid droplets in the cells were visualized with an optical microscope and photographed. The stained lipid droplets were dissolved in 2-propanol, and absorbance at 520 nm was measured to quantify lipid accumulation.

5. Protein Separation and Western Blot

Total proteins were extracted with a RIPA lysis buffer system including phenylmethylsulfonyl fluoride (PMSF), sodium orthovanadate ($Na_3VO_4$) and protease inhibitor cocktail (Santa Cruz Biotechnology) at 4° C. for 30 minutes, and the extracted sample was centrifuged at 16,000×g for 20 minutes. The concentration of total proteins was quantified using a Pierce BCA Protein Assay Kit (Thermo Fisher Scientific). The proteins (30 to 50 μg) were loaded and separated through sodium dodecyl sulfate-polyacrylamide gel electrophoresis (SDS-PAGE), and then blotted with a PVDF membrane (GE Healthcare, Germany). In order to prevent nonspecific binding of the primary antibodies, the membrane was blocked with TBST including 1% non-fat dry milk for 1 hour and 30 minutes at room temperature (RT). Then, the membrane was incubated overnight at 4° C. together with each primary antibody. The secondary antibodies were conjugated with horseradish peroxidase and visualized with an enhanced chemiluminescence detection kit (GE Healthcare). Analysis of density measurement was performed using Image J software.

Figure 5:
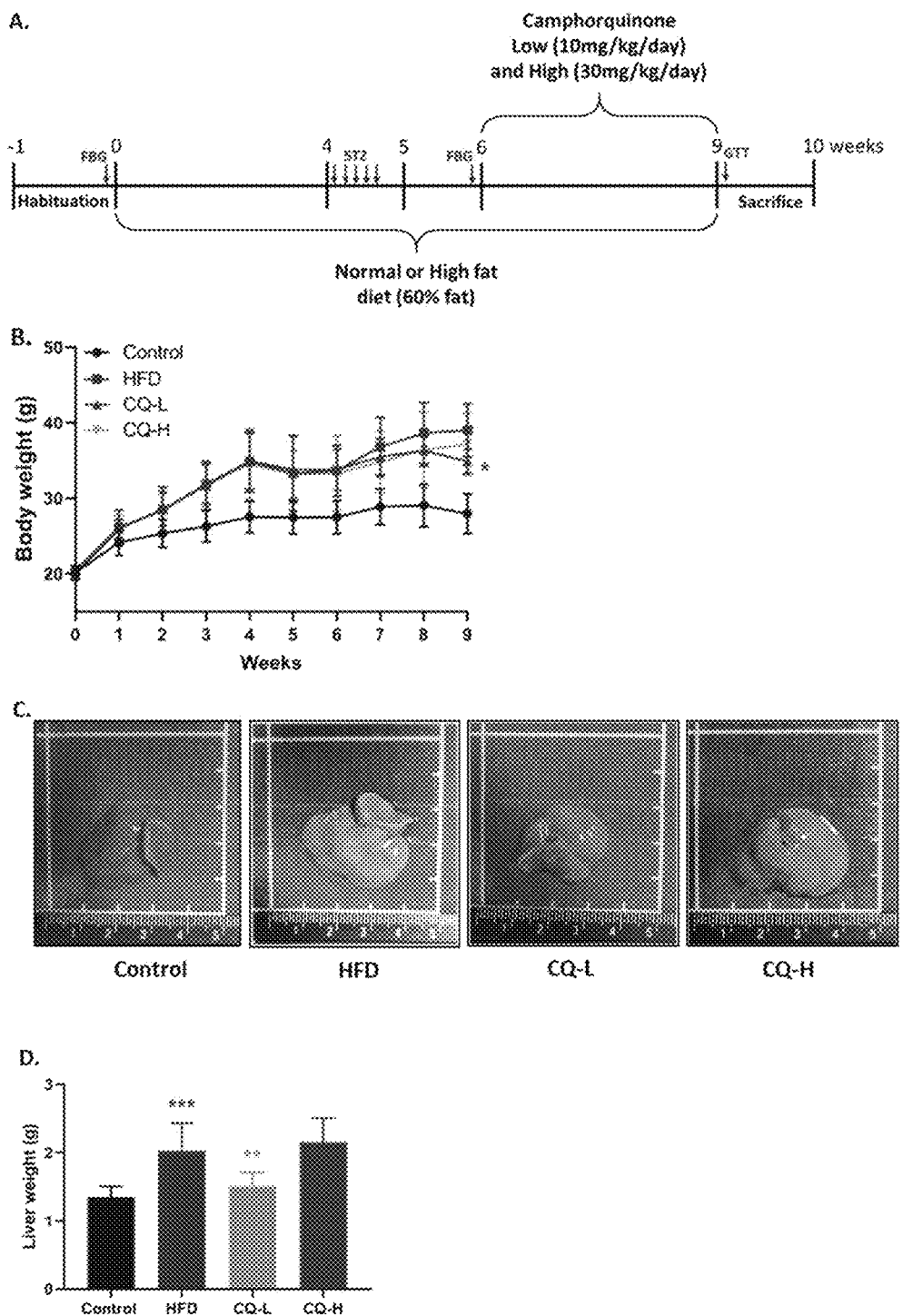
FIG. 5 illustrates confirming effects of decreasing the body weight and liver weight by camphorquinone in a T2D-induced mouse model (diabetic mouse model) (*$P<0.05$, $P<0.01$, *$P<0.001$ and ****$P<0.0001$)

6. Animal Model and Drug Administration 6-week-old male C57BL/6 mice (weight 22±2 g) were purchased from Samtako Bio Korea Co., Ltd. (Osan, Gyeonggi-do, Korea). The mice were maintained at 23 to 25° C. under a 12 h light-dark cycle with free access to food and water in a pathogen-free animal facility center. All animal experiments were approved in accordance with the Chosun University Institutional Animal Care and Use Committee (CIACUC2020-S0009). All animals were fed normal chow pellets (ND, SAM #31, Samtako, Inc.), and went through a period of adjustment for 1 week. During the following week, the animals were randomly classified according to the body weight, and one-third of the animals were classified as normal controls to be fed normal chow pellets throughout the study. On the other hand, the remaining animals were fed a high-fat diet (HFD; 60% Kcal energy as fat) (study diet; #D12492; New Brunswick, NJ 08901 USA) for 2 weeks in order to induce insulin resistance, and the diet was continued until the study ended. Then, STZ (30 mg/kg, i.p.) was administered to the animals for 5 consecutive days from the 4th week to induce T2DM therein. On the other hand, the normal control animals were administered the same volume of citrate buffer instead of the STZ. Blood glucose levels of the animals were measured at the end of week 5, and animals showing a fasting blood glucose level (FBG)≥200 mg/dl were selected for the study. Finally, the animals were divided into the following 4 groups; Group 1: saline-treated normal control mice (Control), Group 2: saline-treated diabetic control mice (HFD), Group 3: camphorquinone (10 mg/kg/day, i.p.)-treated diabetic mice (CQ-L), and Group 4: camphorquinone (30 mg/kg/day, i.p.)-treated diabetic mice (CQ-H). Treatment with saline and camphorquinone (hereinafter, drug treatment) was performed for 3 consecutive weeks. Until the study was completed, Group 1 was fed the normal chow pellets, but Groups 2-4 were fed the high-fat diet (see FIG. 5). Fasting blood glucose level (FBG) and glucose tolerance test (GTT) were performed when 3 weeks have elapsed after drug treatment. Blood samples were taken from retro orbital sinus, and plasma samples were taken by centrifuging blood at 1000 rpm for 5 minutes. The plasma samples were stored at −80° C. for further experiments. At the end of the study, all animals were sacrificed, and liver tissues thereof were immediately separated and frozen, then stored in liquid nitrogen until use them later.

7. Glucose Tolerance Examination

After the four groups of mouse models were fasted overnight, 1.5 g/kg of d-glucose was intraperitoneally injected. To measure fasting blood glucose levels, blood samples were collected from the tails of each mouse at 0, 15, 30, 60, 90, and 120 minutes each after glucose infusion, by using s Green Doctor blood glucose monitoring system (G400; Green Doctor, GC Pharma, Yongin-si, South-Korea).

8. RNA Extraction and Quantitative Reverse Transcription-Polymerase Chain Reaction (qRT-PCR)

Total RNA was separated from liver tissue of the mouse model using RNAisoPlus (Takara). Then, total RNA (2.5 μg) was reverse transcribed using a Primescript™ II 1st strand cDNA synthesis kit (Takara), and quantified using a Power SYBR Green PCR Master mix (Applied BioSystems). Primer pairs are described in Table 1 below. A real-time PCR reaction was performed using a StepOne™ Real-Time PCR system (Applied Bio Systems), and the primer pairs were synthesized in GenoTech (Daejeon, Korea).

TABLE 1

| Gene | Sequence (5'->3') | | PCR product size | Gene accession number |
|---|---|---|---|---|
| CES1 | Forward | GACCCCAGAGAGAGTCAACC (SEQ ID NO: 1) | 132 | >NM_001025195.2 |
|  | Reverse | CTCCTGCTTGTTAATTCCGAC C (SEQ ID NO: 2) | | |
| CES2 | Forward | CTTTCAGCCTGTCCCTAGCA (SEQ ID NO: 3) | 160 | >NM_003869.6 |
|  | Reverse | TGTAGGAGGCAACATCAGCA (SEQ ID NO: 4) | | |
| CPTIA | Forward | GGGCTACAAATTACGTGAGC GA (SEQ ID NO: 5) | 133 | >NM_001876.4 |
|  | Reverse | CTTGCTGCCTGAATGTGAGT (SEQ ID NO: 6) | | |
| MLXIPL1 | Forward | CCTCTTCGAGTGCTTGAGCC (SEQ ID NO: 7) | 156 | >NM_032951.3 |
|  | Reverse | CTCTTCCTCCGCTTCACATAC TG (SEQ ID NO: 8) | | |
| CRTC2 | Forward | GTGTGATGAACCCCAGTCCC (SEQ ID NO: 9) | 90 | >NM_181715.3 |
|  | Reverse | CACCATCCAGAATACCCCCA C (SEQ ID NO: 10) | | |

TABLE 1-continued

| Gene | | Sequence (5'->3') | PCR product size | Gene accession number |
|---|---|---|---|---|
| ACTB | Forward | ATCCGCAAAGACCTGTACGC (SEQ ID NO: 11) | 115 | >NM_001101.5 |
| | Reverse | TCTTCATTGTGCTGGGTGCC (SEQ ID NO: 12) | | |
| Cpt1a | Forward | ATGAGGCTTCCATGACTCGG (SEQ ID NO: 13) | 124 | >NM_013495.2 |
| | Reverse | AACCTCTGCTCTGCCGTTG (SEQ ID NO: 14) | | |
| Cpt1b | Forward | GTTAGCTCTCCTTTCCTGGCT (SEQ ID NO: 15) | 147 | >NM_009948.2 |
| | Reverse | ATCCGCCACGGGACCAAAG (SEQ ID NO: 16) | | |
| Stk11 | Forward | CTGACCTACTCCGAGGGATG (SEQ ID NO: 17) | 134 | >NM_011492.5 |
| | Reverse | GTCTGGGCTTGGTGGGATAG (SEQ ID NO: 18) | | |
| Ppargc1a | Forward | CCCAGAGTCACCAAATGACC (SEQ ID NO: 19) | 113 | >NM_008904.2 |
| | Reverse | GAGGAGTTGTGGGAGGAGTT (SEQ ID NO: 20) | | |
| Fasn | Forward | GACTCGGCTACTGACACGAC (SEQ ID NO: 21) | 123 | >NM_007988.3 |
| | Reverse | CGAGTTGAGCTGGGTTAGGG (SEQ ID NO: 22) | | |
| Srebf1 | Forward | TACAGCGTGGCTGGGAAC (SEQ ID NO: 23) | 140 | >NM_011480.4 |
| | Reverse | GCATCTGAGAACTCCCTGTCT (SEQ ID NO: 24) | | |
| Crtc2 | Forward | GATACCCCCGCCACATTGAC (SEQ ID NO: 25) | 126 | >NM_028881.3 |
| | Reverse | GTCTAAACAACTGCCCCTTCT C (SEQ ID NO: 26) | | |
| Il1α | Forward | CCACCAAAGAACAAAGTCGG G (SEQ ID NO: 27) | 121 | >NM_010554.4 |
| | Reverse | CAGACTGTCAGCACTTCCCA A (SEQ ID NO: 28) | | |
| Il1β | Forward | AAGAGCCCATCCTCTGTGAC T (SEQ ID NO: 29) | 87 | >NM_008361.4 |
| | Reverse | GGAGCCTGTAGTGCAGTTGT (SEQ ID NO: 30) | | |
| Il6 | Forward | AGACAAAGCCAGAGTCCTTC AG (SEQ ID NO: 31) | 110 | >NM_031168.2 |
| | Reverse | GAGCATTGGAAATTGGGGTA GG (SEQ ID NO: 32) | | |
| Trp53 | Forward | GTATTTCACCCTCAAGATCCG C (SEQ ID NO: 33) | 111 | >NM_011640.3 |
| | Reverse | CTGCTGTCTCCAGACTCCTCT (SEQ ID NO: 34) | | |
| Tnf | Forward | GTGCCTATGTCTCAGCCTCTT C (SEQ ID NO: 35) | 118 | >NM_013693.3 |
| | Reverse | GAGGCCATTTGGGAACTTCT CATC (SEQ ID NO: 36) | | |
| Ager | Forward | AGGTGGGGACATGTGTGTC (SEQ ID NO: 37) | 129 | >NM_007425.3 |
| | Reverse | TCTCAGGGTGTCTCCTGGTC (SEQ ID NO: 38) | | |
| Actb | Forward | CCACCATGTACCCAGGCATT (SEQ ID NO: 39) | 189 | >NM_007393.5 |
| | Reverse | CGGACTCATCGTACTCCTGC (SEQ ID NO: 40) | | |

9. Statistical Analysis

All data were represented as mean±standard deviation according to at least 3 or more of biological replicates. A difference between data sets were evaluated by Student's t-test and analysis of variance (ANOVA) together with Holm-Sidak's multiple comparison test using GraphPad Prism (GraphPad Software). Statistical significance levels were represented in the drawings using asterisks as *p<0.05, p<0.01, *p<0.001 and ****p<0.0001.

Experimental Result

1. Confirmation of SIRT1 and AMPK Activation Effects in Hepatocytes

Figure 2:
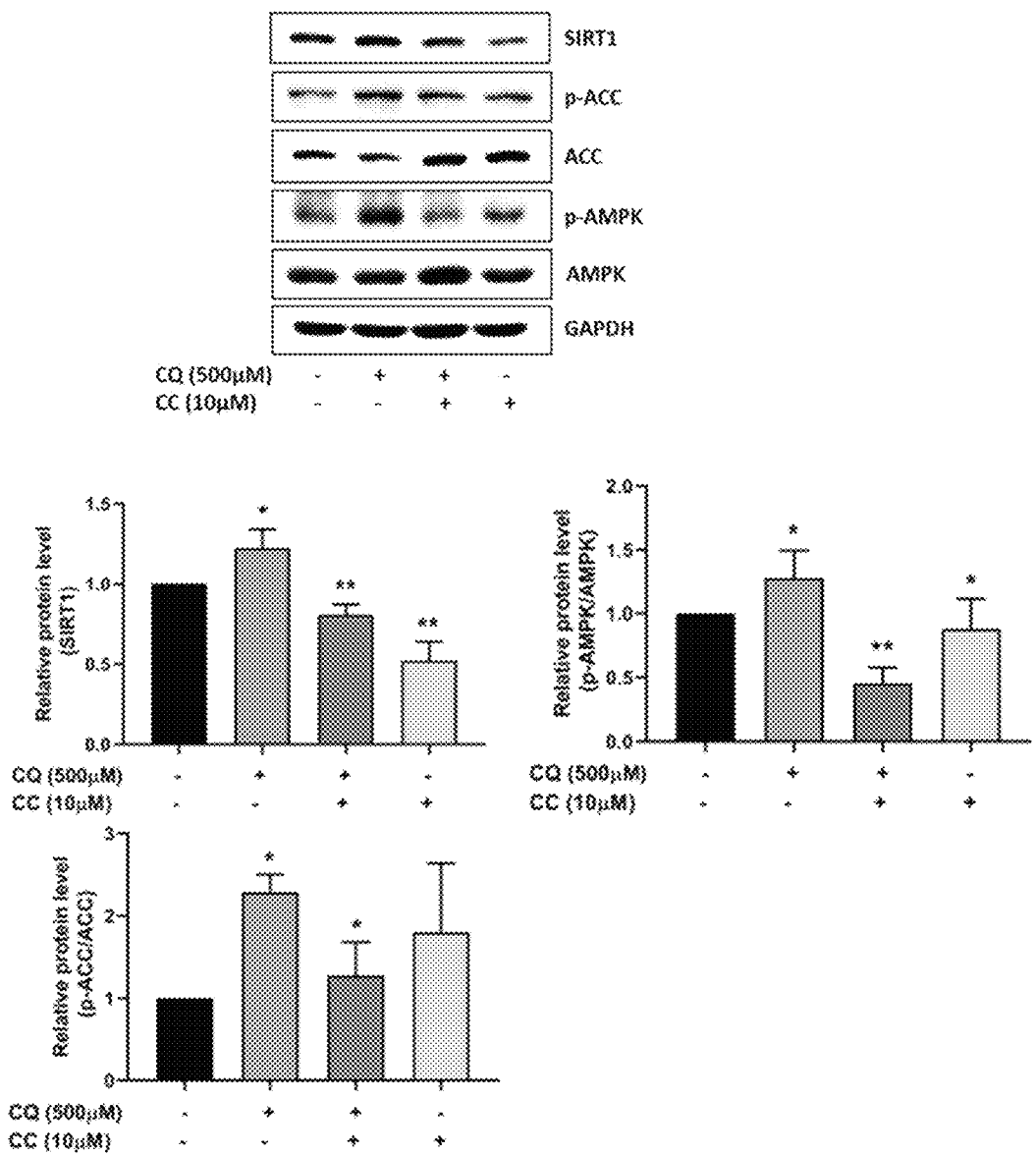
FIG. 2 illustrates results of confirming that Compound C inhibits AMPK, SIRT1 and ACC activated by camphorquinone in HepG2 cells (*$P<0.05$ and **$P<0.01$)

MTT assay was performed to evaluate the cytotoxicity of camphorquinone (CQ) in HepG2 cells. No cytotoxicity was observed up to 500 μM, but cell viability was decreased at a high concentration. Therefore, in vitro experiments were performed using CQ of 500 μM. Activities of SIRT1 and AMPK according to the treatment concentration of CQ in HepG2 cells were measured. SIRT1, AMPK and ACC expressions were significantly increased in a dose-dependent manner of CQ (see FIG. 1). Meanwhile, a significant increase in the expression was observed at 500 μM, but the increased expression was decreased at the high concentration. Next, activation of SIRT1, AMPK and ACC were confirmed using Compound C (CC, AMPK inhibitor). As expected, the expressions of CQ-induced SIRT1, AMPK and ACC proteins in HepG2 cells were significantly decreased by CC treatment (see FIG. 2). The above results suggest that CQ activates the SIRT1, AMPK and ACC in hepatocytes.

2. Confirmation of Effect of Decreasing Lipid Accumulation in Hepatocytes

Figure 3:
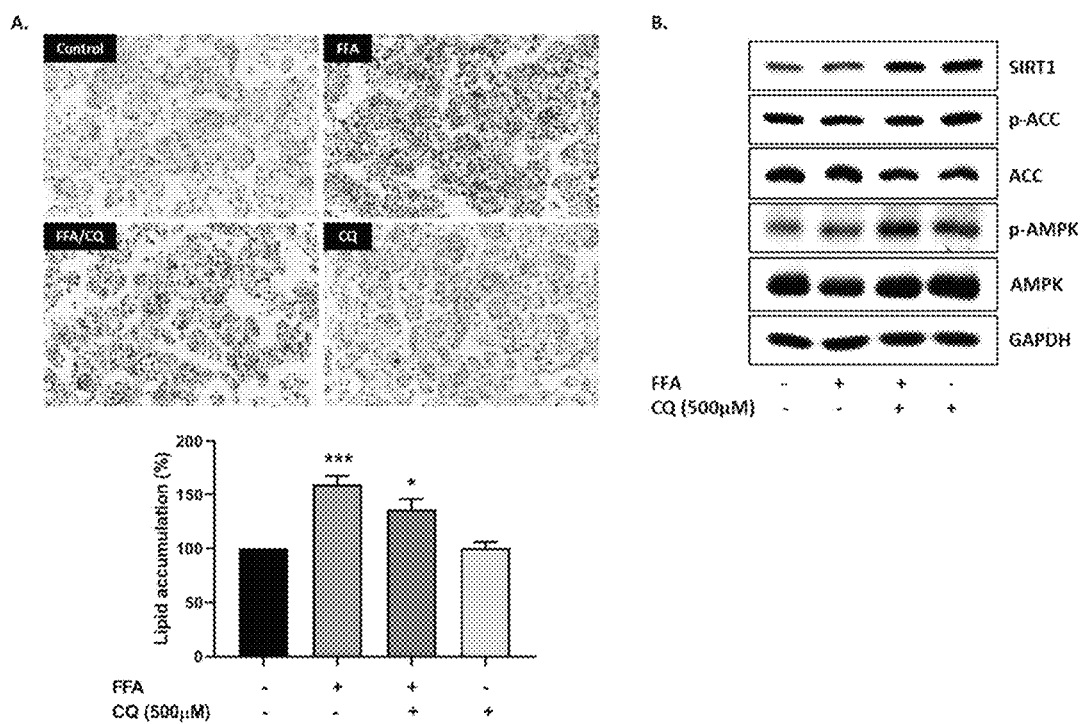
FIG. 3 illustrates results confirming that camphorquinone inhibits the accumulation of lipids in HepG2 cells (*$P<0.05$ and ***$P<0.001$)

An experiment was performed to confirm effects of camphorquinone on lipid accumulation in hepatocytes. Specifically, as described in the previous experimental method '3. Preparation and treatment of stock solution of free fatty acids', lipid accumulation in hepatocytes was induced by FFA treatment (preparation of a fatty hepatocyte model). The treated hepatocytes exhibited that the accumulation of hepatic lipids in FFA-treated HepG2 cells was significantly increased compared to control cells or CQ alone-treated cells (see A of FIG. 3). Meanwhile, it was confirmed that the lipid accumulation was reduced when CQ was treated in FFA-treated HepG2 cells through Oil red O staining.

In addition, expressions of AMPK and SIRT1 in the FFA-treated HepG2 fatty hepatocyte model were investigated. In the FFA-treated hepatocytes, the activation of AMPK, SIRT1 and ACC was restored by CQ (see B of FIG. 3). Through these results, it can be seen that hepatic lipid accumulation in HepG2 cells was effectively decreased by the CQ through the activation of AMPK and SIRT1 pathways.

Figure 4:
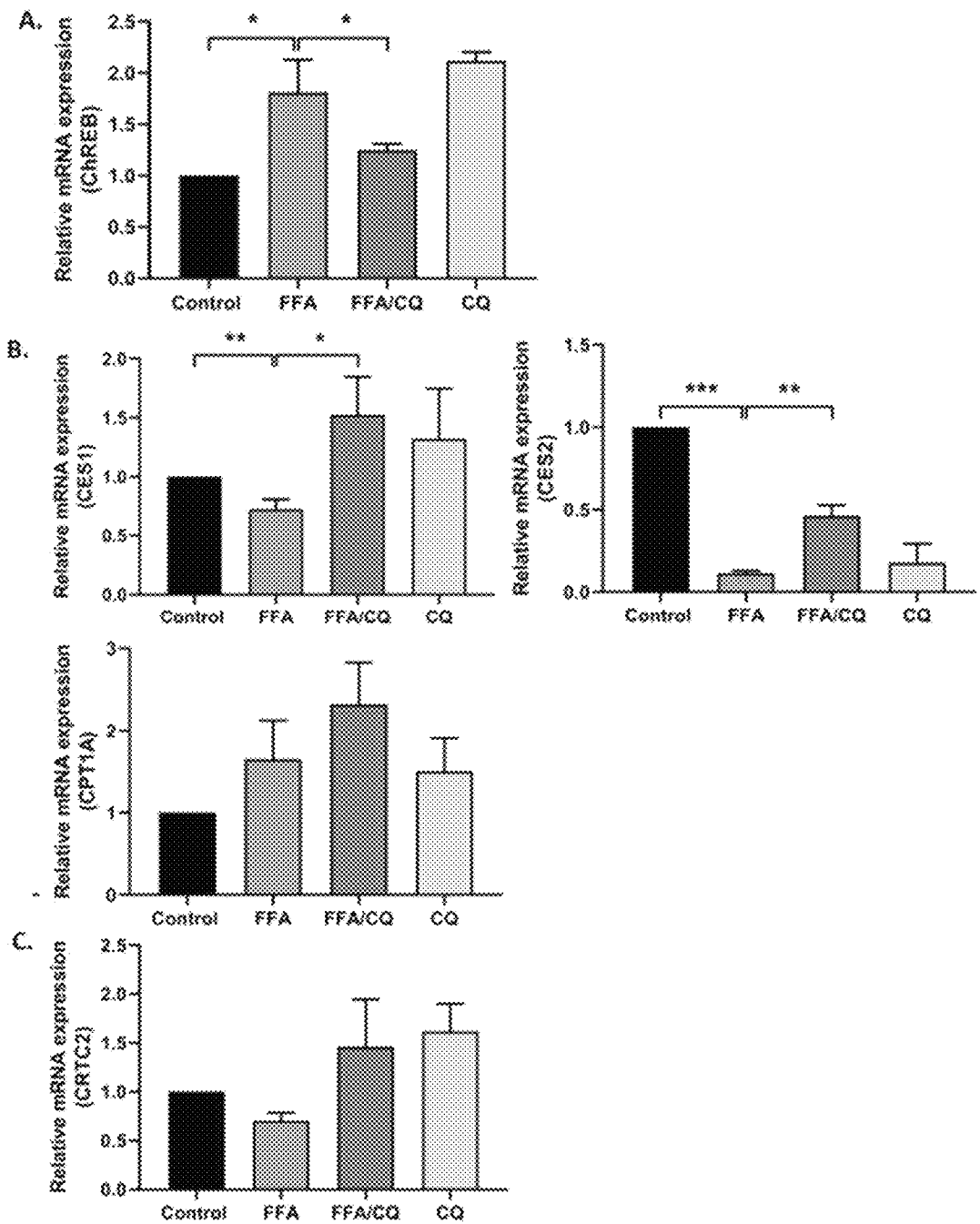
FIG. 4 illustrates results confirming effects of decreasing lipid synthesis and increasing lipid oxidation by camphorquinone in HepG2 cells (*$P<0.05$, $P<0.01$ and *$P<0.001$)

3. Confirmation of Expression Level of Gene Related to Lipid Metabolism in Hepatocytes Gene expression related to fat synthesis and oxidation in the fatty hepatocyte model was analyzed to verify effects of camphorquinone on lipid metabolism. Due to FFA treatment, the expression of lipid synthesis marker (ChREB) was increased and the expressions of lipid β-oxidation markers (CES1, CES2 and CPT1A) were decreased (see A of FIG. 4). Meanwhile, due to treatment of camphorquinone, the expressions of lipid synthesis markers were decreased and the expression of lipid β-oxidation marker was increased in the FFA-treated cell model (see B and C of FIG. 4). The above results suggest that camphorquinone has effects of increasing lipid oxidation and decreasing lipid synthesis in the FFA-treated cell model.

4. Confirmation of Effects of Reducing Body Weight and Improving Glucose Tolerance in Diabetic Mouse Model In order to evaluate whether camphorquinone exerts in vivo therapeutic effects in type 2 diabetic mice, a low concentration of camphorquinone (CQ-L; 10 mg/kg/day, i.p.) and a high concentration of camphorquinone (CQ-H; 30 mg/kg/day, i.p.) were administered to HFD+STZ-induced type 2 diabetic mice, respectively (see A of FIG. 5). In the CQ-L mouse group, the body weight and liver weight were gradually decreased (see B to D of FIG. 5). Next, fasting blood glucose levels were evaluated in the type 2 diabetic mouse model. As expected, the fasting blood glucose levels were significantly increased in the HFD+STZ-treated mice, and were significantly decreased in the CQ-L and CQ-H treated mice.

Figure 6:
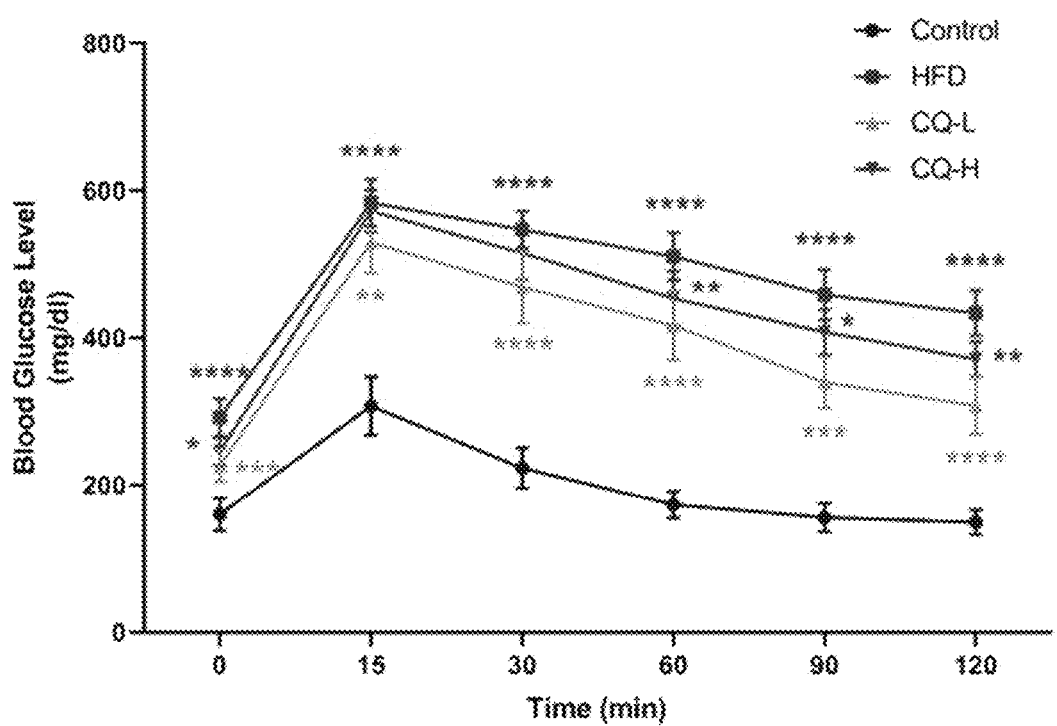
FIG. 6 illustrates confirming effects of reducing blood glucose levels and improving glucose tolerance by camphorquinone in a T2D-induced mouse model (*$P<0.05$, $P<0.01$, *$P<0.001$ and ***$P<0.0001$)

In addition, through confirmation whether or not the blood glucose was lowered within 2 hours after administering the glucose injection to the type 2 diabetic mouse model, glucose tolerance of each mouse was evaluated. It was confirmed that the CQ-L mouse group and the CQ-H mouse group had improved glucose tolerance compared to the mice treated only with HFD+STZ (HFD mouse group) (see FIG. 6). From the above results, it can be seen that the camphorquinone-treated mouse group has excellent effects of reducing the body and liver weights and improving the glucose tolerance compared to a diabetic mouse group (type 2 diabetic mouse model) not treated with camphorquinone.

5. Activation Effects of AMPK and SIRT1 in Liver Tissue of Diabetic Mouse Model

Figure 7:
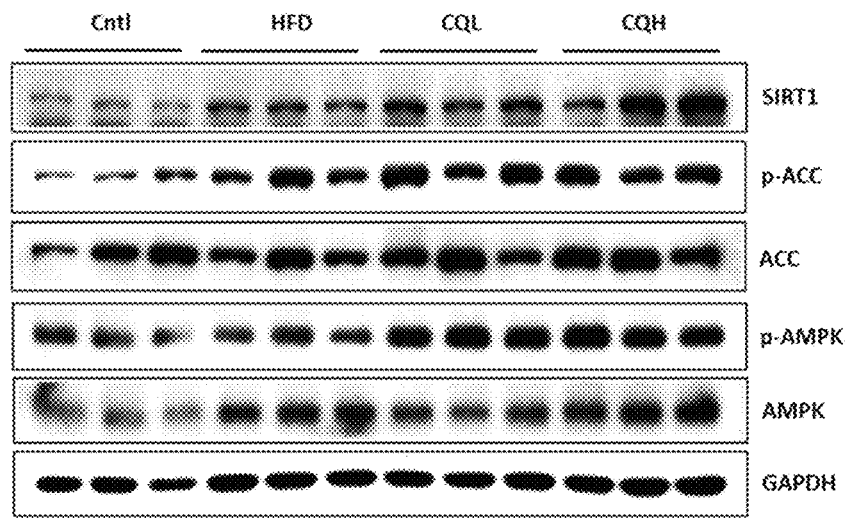
FIG. 7 illustrates confirming effects of enhancing AMPK/SIRT1 pathway activities by camphorquinone in a liver tissue of the T2D-induced mouse model by performing immunoblotting (*$P<0.05$, $P<0.01$ and *$P<0.001$)
Figure 7:
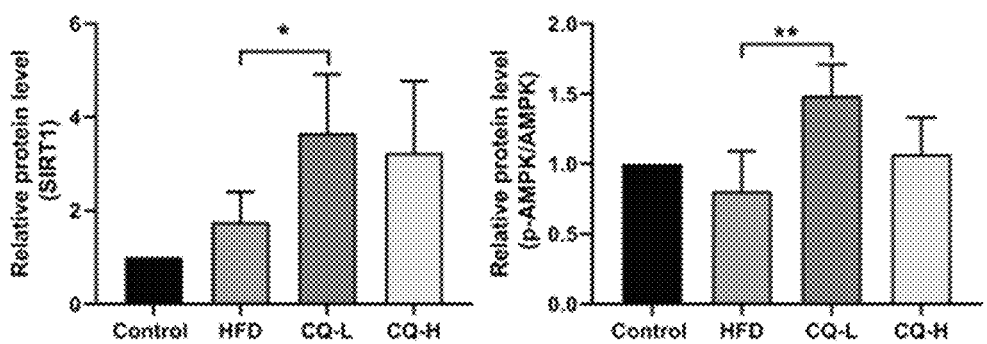
Figure 7:
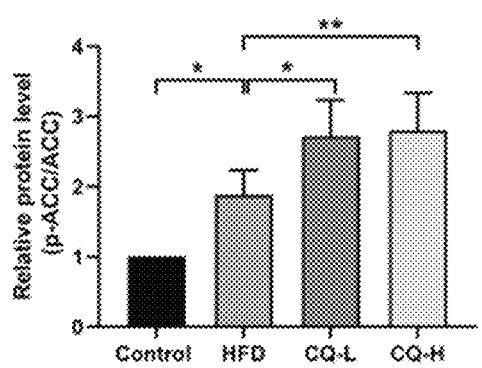

An increased glucose level is an early indicator of obesity-induced type 2 diabetes, which is a promising risk factor for NAFLD. Since it is known that the AMPK and SIRT1 pathways are capable of decreasing the hepatic lipid accumulation, the expressions of AMPK and SIRT1 in the mouse liver tissue were evaluated. In the CQ-treated mice (CQ-L mouse group, and CQ-H mouse group), AMPK and SIRT1 are activated compared to HFD+STZ-treated mice (HFD mouse group) (see FIG. 7).

6. Effect of Increasing LKB1 and ERK Signals in Diabetic Mouse Model

Figure 8:
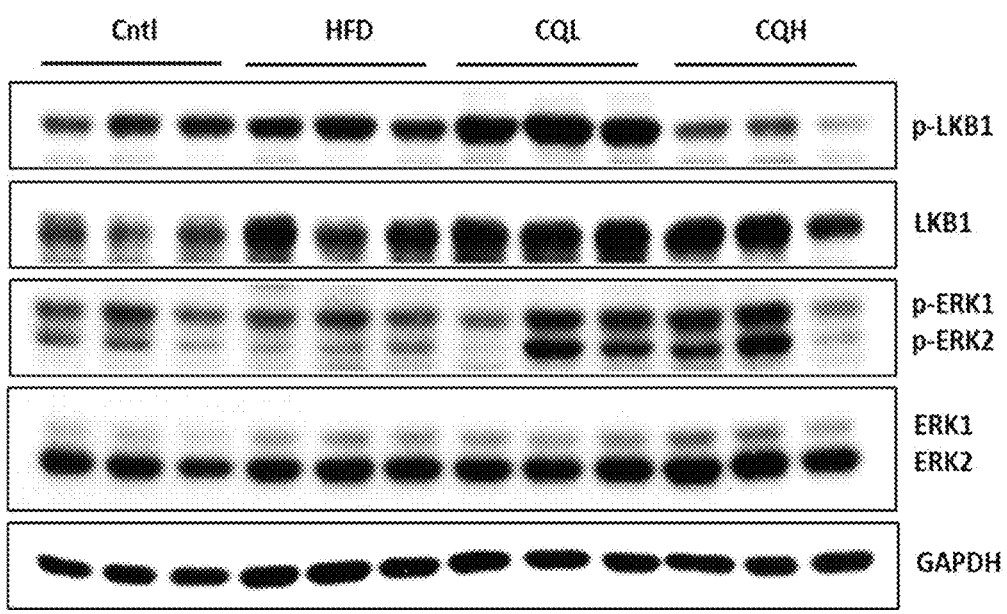
FIG. 8 illustrates confirming whether LKB1/ERK are activated by camphorquinone in the liver tissue of the T2D-induced mouse model.

Next, LKB1 and ERK, which are upstream targets of AMPK activation, were investigated. As compared to the control diabetic mouse model (HFD mouse group), LKB1 and ERK markers were highly expressed in the CQ-L mouse group and the CQ-H mouse group (see FIG. 8). These results indicate that camphorquinone activates LKB1 and ERK-mediated SIRT1/AMPK pathways in the liver tissue.

Figure 9:
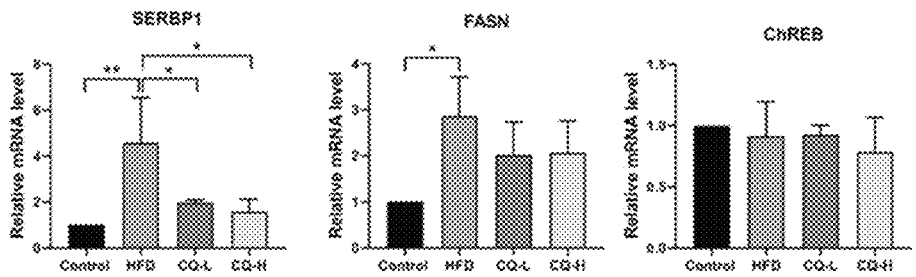
FIG. 9 illustrates confirming effects on lipid metabolism and liver inflammation by camphorquinone in the liver tissue of the T2D-induced mouse model (*$P<0.05$, $P<0.01$, *$P<0.001$ and ***$P<0.0001$)
Figure 9:
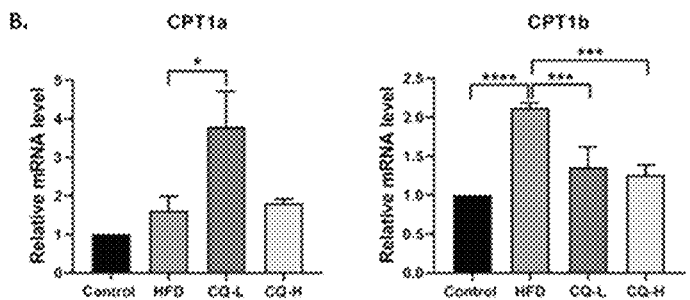
Figure 9:
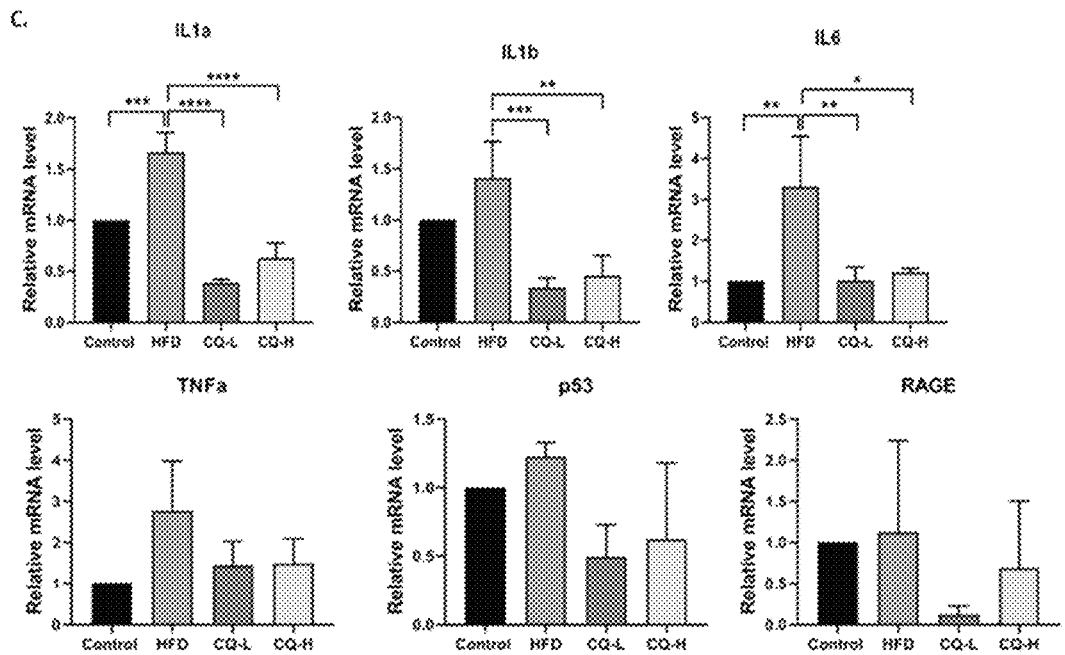

7. Effects of Increasing Lipid Oxidation, and Decreasing Lipid Synthesis and Inflammation in Liver Tissue of Diabetic Mouse Model Expression levels of lipid production-related genes (SREBP1, FASN and ChREB) and β-oxidation-related genes (CPT1a and CPT1b) relevant to hepatic lipid metabolism were evaluated in the diabetic mouse model. As a result, the expressions of SREBP1 and FASN related to lipid production were significantly increased in the HFD mouse group treated with HFD+STZ. On the other hand, in the CQ-L mouse group, the expressions of SREBP1 and FASN were significantly decreased (see A of FIG. 9), and the expression of the lipid β-oxidation gene CPTa was significantly increased in the CQ-L-treated mice (see B of FIG. 9).

Figure 10:
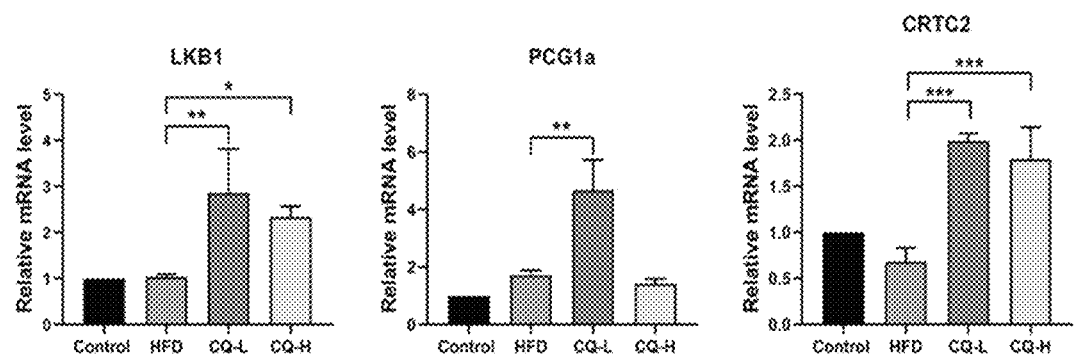
FIG. 10 illustrates confirming that camphorquinone activates LKB1, PGC1α and CRTC2, which are upstream signals of AMPK, in the liver tissue of the T2D-induced mouse model (*$P<0.05$, $P<0.01$ and *$P<0.001$).

In addition, expression levels of inflammatory markers in the liver such as IL1α, IL1β, IL6, p53, TNFα and RAGE were evaluated. As compared to the HFD+STZ-treated HFD mouse group, the expressions of most inflammatory markers were significantly decreased in the CQ-L-treated mouse group (see C of FIG. 9). Further, expression levels of LKB1, PGC1a and CRTC2 were evaluated in the diabetic mouse models. The expressions of these markers were increased upon CQ treatment compared with the HFD+STZ-treated HFD mouse group (see FIG. 10). These results suggest that treatment with camphorquinone may potentially increase β-oxidation and decrease adipogenesis and inflammation in the diabetic mouse model.

REFERENCE TO AN ELECTRONIC SEQUENCE LISTING

A sequence listing electronically submitted on Oct. 17, 2022 as a XML file named 20221017_Q99222LC79_TU_SEQ.XML, created on Oct. 14, 2022 and having a size of 51,670 bytes, is incorporated herein by reference in its entirety.

What is claimed is:

1. A method for treating metabolic diseases, the method comprising administering a composition comprising a compound represented by Formula 1 below or a pharmaceutically acceptable salt thereof to a subject in need thereof:

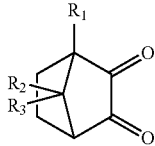

[Formula 1]

wherein $R_1$ is H or C1 to C6 alkyl;

$R_2$ is H or C1 to C6 alkyl; and $R_3$ is H or C1 to C6 alkyl, wherein the metabolic disease is selected from the group consisting of obesity, diabetes, dyslipidemia, fatty liver, arteriosclerosis, stroke, hyperglycemia, insulin resistance disease and hyperinsulinemia.

2. The method of claim 1, wherein R1 is C1 alkyl, R2 is C1 alkyl, and R3 is C1 alkyl.

3. A method for reducing body weight or liver weight, the method comprising administering a food composition comprising a compound represented by Formula 1 below or a sitologically acceptable salt thereof to a subject in need thereof:

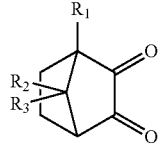

[Formula 1]

wherein $R_1$ is H or C1 to C6 alkyl;

$R_2$ is H or C1 to C6 alkyl; and $R_3$ is H or C1 to C6 alkyl.

4. A method for reducing blood glucose level or improving glucose tolerance, the method comprising administering a food composition comprising a compound represented by Formula 1 below or a sitologically acceptable salt thereof to a subject in need thereof:

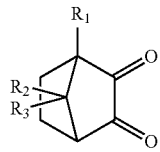

[Formula 1]

wherein $R_1$ is H or C1 to C6 alkyl;

$R_2$ is H or C1 to C6 alkyl; and $R_3$ is H or C1 to C6 alkyl.

* * * * *

```
                            SEQUENCE LISTING

Sequence total quantity: 40
SEQ ID NO: 1            moltype = DNA  length = 20
FEATURE                 Location/Qualifiers
misc_feature            1..20
                        note = CES1 forward primer
source                  1..20
                        mol_type = other DNA
                        organism = synthetic construct
SEQUENCE: 1
gacccagag agagtcaacc                                                  20

SEQ ID NO: 2            moltype = DNA  length = 22
FEATURE                 Location/Qualifiers
misc_feature            1..22
                        note = CES1 reverse primer
source                  1..22
                        mol_type = other DNA
                        organism = synthetic construct
SEQUENCE: 2
ctcctgcttg ttaattccga cc                                              22

SEQ ID NO: 3            moltype = DNA  length = 20
FEATURE                 Location/Qualifiers
misc_feature            1..20
                        note = CES2 forward primer
source                  1..20
                        mol_type = other DNA
                        organism = synthetic construct
SEQUENCE: 3
ctttcagcct gtccctagca                                                 20

SEQ ID NO: 4            moltype = DNA  length = 20
FEATURE                 Location/Qualifiers
misc_feature            1..20
                        note = CES2 reverse primer
source                  1..20
                        mol_type = other DNA
                        organism = synthetic construct
SEQUENCE: 4
tgtaggaggc aacatcagca                                                 20

SEQ ID NO: 5            moltype = DNA  length = 22
FEATURE                 Location/Qualifiers
misc_feature            1..22
                        note = CPT1A forward primer
source                  1..22
                        mol_type = other DNA
                        organism = synthetic construct
SEQUENCE: 5
gggctacaaa ttacgtgagc ga                                              22

SEQ ID NO: 6            moltype = DNA  length = 20
FEATURE                 Location/Qualifiers
misc_feature            1..20
                        note = CPT1A reverse primer
source                  1..20
                        mol_type = other DNA
                        organism = synthetic construct
SEQUENCE: 6
cttgctgcct gaatgtgagt                                                 20

SEQ ID NO: 7            moltype = DNA  length = 20
FEATURE                 Location/Qualifiers
misc_feature            1..20
                        note = MLXIPL1 forward primer
```

```
source                   1..20
                         mol_type = other DNA
                         organism = synthetic construct
SEQUENCE: 7
cctcttcgag tgcttgagcc                                                    20

SEQ ID NO: 8             moltype = DNA   length = 23
FEATURE                  Location/Qualifiers
misc_feature             1..23
                         note = MLXIPL1 reverse primer
source                   1..23
                         mol_type = other DNA
                         organism = synthetic construct
SEQUENCE: 8
ctcttcctcc gcttcacata ctg                                                23

SEQ ID NO: 9             moltype = DNA   length = 20
FEATURE                  Location/Qualifiers
misc_feature             1..20
                         note = CRTC2 forward primer
source                   1..20
                         mol_type = other DNA
                         organism = synthetic construct
SEQUENCE: 9
gtgtgatgaa ccccagtccc                                                    20

SEQ ID NO: 10            moltype = DNA   length = 21
FEATURE                  Location/Qualifiers
misc_feature             1..21
                         note = CRTC2 reverse primer
source                   1..21
                         mol_type = other DNA
                         organism = synthetic construct
SEQUENCE: 10
caccatccag aataccccca c                                                  21

SEQ ID NO: 11            moltype = DNA   length = 20
FEATURE                  Location/Qualifiers
misc_feature             1..20
                         note = ACTB forward primer
source                   1..20
                         mol_type = other DNA
                         organism = synthetic construct
SEQUENCE: 11
atccgcaaag acctgtacgc                                                    20

SEQ ID NO: 12            moltype = DNA   length = 20
FEATURE                  Location/Qualifiers
misc_feature             1..20
                         note = ACTB reverse primer
source                   1..20
                         mol_type = other DNA
                         organism = synthetic construct
SEQUENCE: 12
tcttcattgt gctgggtgcc                                                    20

SEQ ID NO: 13            moltype = DNA   length = 20
FEATURE                  Location/Qualifiers
misc_feature             1..20
                         note = Cpt1a forward primer
source                   1..20
                         mol_type = other DNA
                         organism = synthetic construct
SEQUENCE: 13
atgaggcttc catgactcgg                                                    20

SEQ ID NO: 14            moltype = DNA   length = 19
FEATURE                  Location/Qualifiers
misc_feature             1..19
                         note = Cpt1a reverse primer
source                   1..19
                         mol_type = other DNA
                         organism = synthetic construct
SEQUENCE: 14
aacctctgct ctgccgttg                                                     19

SEQ ID NO: 15            moltype = DNA   length = 21
FEATURE                  Location/Qualifiers
misc_feature             1..21
```

```
                        note = Cpt1b forward primer
source                  1..21
                        mol_type = other DNA
                        organism = synthetic construct
SEQUENCE: 15
gttagctctc ctttcctggc t                                              21

SEQ ID NO: 16           moltype = DNA  length = 19
FEATURE                 Location/Qualifiers
misc_feature            1..19
                        note = Cpt1b reverse primer
source                  1..19
                        mol_type = other DNA
                        organism = synthetic construct
SEQUENCE: 16
atccgccacg ggaccaaag                                                 19

SEQ ID NO: 17           moltype = DNA  length = 20
FEATURE                 Location/Qualifiers
misc_feature            1..20
                        note = Stk11 forward primer
source                  1..20
                        mol_type = other DNA
                        organism = synthetic construct
SEQUENCE: 17
ctgacctact ccgagggatg                                                20

SEQ ID NO: 18           moltype = DNA  length = 20
FEATURE                 Location/Qualifiers
misc_feature            1..20
                        note = Stk11 reverse primer
source                  1..20
                        mol_type = other DNA
                        organism = synthetic construct
SEQUENCE: 18
gtctgggctt ggtgggatag                                                20

SEQ ID NO: 19           moltype = DNA  length = 20
FEATURE                 Location/Qualifiers
misc_feature            1..20
                        note = Ppargc1a forward primer
source                  1..20
                        mol_type = other DNA
                        organism = synthetic construct
SEQUENCE: 19
cccagagtca ccaaatgacc                                                20

SEQ ID NO: 20           moltype = DNA  length = 20
FEATURE                 Location/Qualifiers
misc_feature            1..20
                        note = Ppargc1a reverse primer
source                  1..20
                        mol_type = other DNA
                        organism = synthetic construct
SEQUENCE: 20
gaggagttgt gggaggagtt                                                20

SEQ ID NO: 21           moltype = DNA  length = 20
FEATURE                 Location/Qualifiers
misc_feature            1..20
                        note = Fasn forward primer
source                  1..20
                        mol_type = other DNA
                        organism = synthetic construct
SEQUENCE: 21
gactcggcta ctgacacgac                                                20

SEQ ID NO: 22           moltype = DNA  length = 20
FEATURE                 Location/Qualifiers
misc_feature            1..20
                        note = Fasn reverse primer
source                  1..20
                        mol_type = other DNA
                        organism = synthetic construct
SEQUENCE: 22
cgagttgagc tgggttaggg                                                20

SEQ ID NO: 23           moltype = DNA  length = 18
FEATURE                 Location/Qualifiers
```

```
misc_feature              1..18
                          note = Srebf1 forward primer
source                    1..18
                          mol_type = other DNA
                          organism = synthetic construct
SEQUENCE: 23
tacagcgtgg ctgggaac                                                         18

SEQ ID NO: 24             moltype = DNA  length = 21
FEATURE                   Location/Qualifiers
misc_feature              1..21
                          note = Srebf1 reverse primer
source                    1..21
                          mol_type = other DNA
                          organism = synthetic construct
SEQUENCE: 24
gcatctgaga actccctgtc t                                                     21

SEQ ID NO: 25             moltype = DNA  length = 20
FEATURE                   Location/Qualifiers
misc_feature              1..20
                          note = Crtc2 forward primer
source                    1..20
                          mol_type = other DNA
                          organism = synthetic construct
SEQUENCE: 25
gataccccg ccacattgac                                                        20

SEQ ID NO: 26             moltype = DNA  length = 22
FEATURE                   Location/Qualifiers
misc_feature              1..22
                          note = Crtc2 reverse primer
source                    1..22
                          mol_type = other DNA
                          organism = synthetic construct
SEQUENCE: 26
gtctaaacaa ctgccccttc tc                                                    22

SEQ ID NO: 27             moltype = DNA  length = 21
FEATURE                   Location/Qualifiers
misc_feature              1..21
                          note = IL1 alpha forward primer
source                    1..21
                          mol_type = other DNA
                          organism = synthetic construct
SEQUENCE: 27
ccaccaaaga acaaagtcgg g                                                     21

SEQ ID NO: 28             moltype = DNA  length = 21
FEATURE                   Location/Qualifiers
misc_feature              1..21
                          note = IL1 alpha reverse primer
source                    1..21
                          mol_type = other DNA
                          organism = synthetic construct
SEQUENCE: 28
cagactgtca gcacttccca a                                                     21

SEQ ID NO: 29             moltype = DNA  length = 21
FEATURE                   Location/Qualifiers
misc_feature              1..21
                          note = IL1 beta forward primer
source                    1..21
                          mol_type = other DNA
                          organism = synthetic construct
SEQUENCE: 29
aagagcccat cctctgtgac t                                                     21

SEQ ID NO: 30             moltype = DNA  length = 20
FEATURE                   Location/Qualifiers
misc_feature              1..20
                          note = IL1 beta reverse primer
source                    1..20
                          mol_type = other DNA
                          organism = synthetic construct
SEQUENCE: 30
ggagcctgta gtgcagttgt                                                       20

SEQ ID NO: 31             moltype = DNA  length = 22
```

```
FEATURE                 Location/Qualifiers
misc_feature            1..22
                        note = IL6 forward primer
source                  1..22
                        mol_type = other DNA
                        organism = synthetic construct
SEQUENCE: 31
agacaaagcc agagtccttc ag                                                  22

SEQ ID NO: 32           moltype = DNA  length = 22
FEATURE                 Location/Qualifiers
misc_feature            1..22
                        note = IL6 reverse primer
source                  1..22
                        mol_type = other DNA
                        organism = synthetic construct
SEQUENCE: 32
gagcattgga aattggggta gg                                                  22

SEQ ID NO: 33           moltype = DNA  length = 22
FEATURE                 Location/Qualifiers
misc_feature            1..22
                        note = Trp53 forward primer
source                  1..22
                        mol_type = other DNA
                        organism = synthetic construct
SEQUENCE: 33
gtatttcacc ctcaagatcc gc                                                  22

SEQ ID NO: 34           moltype = DNA  length = 21
FEATURE                 Location/Qualifiers
misc_feature            1..21
                        note = Trp53 reverse primer
source                  1..21
                        mol_type = other DNA
                        organism = synthetic construct
SEQUENCE: 34
ctgctgtctc cagactcctc t                                                   21

SEQ ID NO: 35           moltype = DNA  length = 22
FEATURE                 Location/Qualifiers
misc_feature            1..22
                        note = Tnf forward primer
source                  1..22
                        mol_type = other DNA
                        organism = synthetic construct
SEQUENCE: 35
gtgcctatgt ctcagcctct tc                                                  22

SEQ ID NO: 36           moltype = DNA  length = 24
FEATURE                 Location/Qualifiers
misc_feature            1..24
                        note = Tnf reverse primer
source                  1..24
                        mol_type = other DNA
                        organism = synthetic construct
SEQUENCE: 36
gaggccattt gggaacttct catc                                                24

SEQ ID NO: 37           moltype = DNA  length = 19
FEATURE                 Location/Qualifiers
misc_feature            1..19
                        note = Ager forward primer
source                  1..19
                        mol_type = other DNA
                        organism = synthetic construct
SEQUENCE: 37
aggtggggac atgtgtgtc                                                      19

SEQ ID NO: 38           moltype = DNA  length = 20
FEATURE                 Location/Qualifiers
misc_feature            1..20
                        note = Ager reverse primer
source                  1..20
                        mol_type = other DNA
                        organism = synthetic construct
SEQUENCE: 38
tctcagggtg tctcctggtc                                                     20
```

-continued

```
SEQ ID NO: 39          moltype = DNA  length = 20
FEATURE                Location/Qualifiers
misc_feature           1..20
                       note = Actb forward primer
source                 1..20
                       mol_type = other DNA
                       organism = synthetic construct
SEQUENCE: 39
ccaccatgta cccaggcatt                                                 20

SEQ ID NO: 40          moltype = DNA  length = 20
FEATURE                Location/Qualifiers
misc_feature           1..20
                       note = Actb reverse primer
source                 1..20
                       mol_type = other DNA
                       organism = synthetic construct
SEQUENCE: 40
cggactcatc gtactcctgc                                                 20
```